(12) United States Patent
Farrar et al.

(10) Patent No.: US 9,572,941 B2
(45) Date of Patent: Feb. 21, 2017

(54) NEEDLE PROTECTION DEVICE WITH GAUGE SPECIFIC COLOR CODING AND METHOD FOR MANUFACTURING THEREOF

(75) Inventors: Quinton Farrar, Keene, NH (US); Frank Blinkhorn, Keene, NH (US); Roddi James Simpson, Higganum, CT (US); Steven H. Nguyen, Cypress, TX (US)

(73) Assignee: SMITHS MEDICAL ASD, INC., Plymouth, MN (US)

( * ) Notice: Subject to any disclaimer, the term of this patent is extended or adjusted under 35 U.S.C. 154(b) by 721 days.

(21) Appl. No.: 11/783,378

(22) Filed: Apr. 9, 2007

(65) Prior Publication Data
US 2007/0208311 A1   Sep. 6, 2007

Related U.S. Application Data

(60) Division of application No. 10/925,962, filed on Aug. 26, 2004, now abandoned, which is a
(Continued)

(51) Int. Cl.
*A61M 5/00* (2006.01)
*A61M 5/32* (2006.01)
*A61M 5/31* (2006.01)

(52) U.S. Cl.
CPC .......... *A61M 5/3216* (2013.01); *A61M 5/3129* (2013.01); *A61M 5/3202* (2013.01); *A61M 5/32* (2013.01); *A61M 2205/6081* (2013.01)

(58) Field of Classification Search
CPC ..................... A61M 2205/584; A61M 5/3129; A61M 5/3216; A61M 5/3202; A61M 5/32; A61M 2205/6081
(Continued)

(56) References Cited

U.S. PATENT DOCUMENTS 3,658,061 A * 4/1972 Hall ........................... 604/263
3,728,184 A   4/1973 Burke et al.
(Continued)

FOREIGN PATENT DOCUMENTS

CA   2077742   3/1994
CA   2157999   8/1999
(Continued)

OTHER PUBLICATIONS

Supplementary European Search Report, Jan. 3, 2012.
Dansk Standard DS/EN ISO 7864, 1994, "Sterile hypodermic needles for single use".

*Primary Examiner* — Theodore Stigell
(74) *Attorney, Agent, or Firm* — Louis Woo

(57) ABSTRACT

To enable a user to readily determine the gauge of the needle of a needle assembly that has a base and a needle protective housing pivotably attached thereto, the needle assembly is injection molded from a color coded molding material which color was preassigned to correspond to the gauge of the needle. As a result, both the base and the protective housing of the needle assembly have the same specific color, and reflect or provide an indication of the given gauge of the needle. The needle sheath that covers the needle prior to use may be made of a plastics material that may be clear, or have the same or a different color than that of the needle assembly. The gauge of the needle of a fixed needle syringe could also be ascertained by its color coded needle protective housing. Color coded markings that correspond to the gauge of the needle may also be printed onto the syringe barrel of the fixed needle syringe.

18 Claims, 5 Drawing Sheets

Related U.S. Application Data continuation-in-part of application No. 10/751,982, filed on Jan. 7, 2004, now abandoned.

(58) Field of Classification Search
USPC ............. 604/263, 181, 198, 111, 189, 192
See application file for complete search history.

(56) References Cited

U.S. PATENT DOCUMENTS

| | | | |
|---|---|---|---|
| 4,034,755 A | 7/1977 | Schultz | |
| 4,551,138 A | 11/1985 | Shinohara | |
| 4,909,792 A | 3/1990 | Norelli | |
| 4,982,842 A * | 1/1991 | Hollister | 206/365 |
| 4,994,046 A | 2/1991 | Wesson et al. | |
| 5,015,241 A * | 5/1991 | Feimer | 604/198 |
| 5,085,640 A | 2/1992 | Gibbs | |
| 5,147,319 A | 9/1992 | Ishikawa et al. | |
| 5,232,455 A * | 8/1993 | Hollister | 604/192 |
| 5,328,466 A * | 7/1994 | Demark | 604/189 |
| 5,338,311 A | 8/1994 | Mahurkar | |
| 5,584,816 A | 12/1996 | Gyure et al. | |
| 5,599,318 A * | 2/1997 | Sweeney et al. | 604/263 |
| 5,662,617 A | 9/1997 | Odell et al. | |
| 5,868,716 A * | 2/1999 | Sweeney et al. | 604/263 |
| 5,993,426 A | 11/1999 | Hollister | |
| 6,096,065 A | 8/2000 | Crowley | |
| 6,156,012 A | 12/2000 | Nathan | |
| 6,192,568 B1 | 2/2001 | Kafrawy et al. | |
| RE37,110 E * | 3/2001 | Hollister | 206/365 |
| 6,413,243 B1 | 7/2002 | Geist | |
| 6,524,281 B1 | 2/2003 | Hudon | |
| 6,582,397 B2 | 6/2003 | Alesi et al. | |
| 6,663,601 B2 * | 12/2003 | Hetzler et al. | 604/181 |
| 2002/0052577 A1 * | 5/2002 | Shimazaki | 604/192 |
| 2003/0036732 A1 | 2/2003 | Marano-Ford | |
| 2003/0212369 A1 | 11/2003 | Kobayashi | |
| 2004/0186437 A1 * | 9/2004 | Frenette et al. | 604/189 |
| 2005/0054986 A1 * | 3/2005 | Simpson | 604/192 |
| 2005/0065482 A1 * | 3/2005 | Hauri et al. | 604/263 |
| 2007/0179451 A1 * | 8/2007 | Sprinkle et al. | 604/192 |

FOREIGN PATENT DOCUMENTS

| | | |
|---|---|---|
| CA | 2174828 | 12/1999 |
| CA | 2405816 | 10/2001 |
| CA | 2712327 | 12/2002 |
| GB | 893569 A | 4/1962 |

\* cited by examiner

NEEDLE PROTECTION DEVICE WITH GAUGE SPECIFIC COLOR CODING AND METHOD FOR MANUFACTURING THEREOF

This application is a continuation-in-part of application Ser. No. 10/751,982 filed on Jan. 7, 2004.

FIELD OF THE INVENTION

The present invention relates to needle assemblies and specifically needle assemblies that have a protective housing connected to a base, with a color scheme for the needle assembly that relates to the gauge of the needle of the needle assembly.

BACKGROUND OF THE INVENTION

In a medical environment, to draw blood from or inject fluid to a patient, in the case of a syringe being used, conventionally a needle is mated to the syringe by way of a hub to which the needle is attached or integrated. Depending on the procedure, the gauge of the needle tends to vary. It is well established that the gauge of the needle may be determined by the color of the hub. Yet the needle hub, or at least a portion thereof, is often hidden by the needle sheath that covers the needle when the needle is mated to the luer of the syringe.

With current technological and safety advances, a needle protective housing may be attached to the needle hub, with the needle hub, or base, and the needle protective housing being joined and either acting as an adapter as taught by U.S. Pat. No. 4,982,842, or as a single unit with the needle integrated to the base and the needle protective housing connected to the base as disclosed in U.S. Pat. No. 5,993,426 and U.S. Pat. RE37,110. There are also instances where a needle protective housing may be connected to a syringe, as disclosed by U.S. Pat. Nos. 5,232,455, 6,582,397, and application Ser. Nos. 10/657,171 and 29/189,589, both filed on Sep. 9, 2003. The respective disclosures of the '842, '426, '110, '455, and '397 patents and the '171 and '589 applications are incorporated by reference herein.

In the devices disclosed by the aforenoted patents as well as in the prior art, there has not been any established scheme that allows a user to readily determine the gauge of the needle she is using. And given that the use of a needle with a particular gauge may well be of import in an emergency situation, there is a need to provide a scheme whereby a user can readily ascertain the gauge of the needle she would like to use without having to directly look at the needle, which oftentimes is difficult since the needle is usually covered by a sheath prior to use.

SUMMARY OF THE INVENTION

To enable a user to readily determine the needle gauge of a needle assembly that has a housing attached to a base or a needle hub to which the needle is attached, during the manufacturing process, color pigmentation that is specific to the gauge of the needle is added to the mold material, which most likely would be a plastics material such as polypropylene. With the mold material having the color that corresponds to the gauge of the needle in accordance with the ISO (International Standard Organization) standard, a user could readily pick out from among a plurality of needle assemblies the particular gauge of needle she wants to use. For example, a needle assembly with both the base and the housing being black would signify to the user that it is a 22 gauge (22G) needle, while a blue needle assembly would indicate to the user a 23G needle is in that blue needle assembly.

To provide a redundant or back up check for the user to determine the gauge of the needle for the needle assembly, the needle sheath that covers the needle prior to use may be made of clear plastic, so that the user can ascertain the gauge the needle visually, and confirm it with the color scheme of the needle assembly, or vis versa. Alternatively, the needle sheath may be manufactured to have the same color as the needle protection housing.

The needle device or needle assembly of the instant invention has a needle of a particular gauge and a base having attached thereto a needle protection housing that is pivotable relative to the base. Both the base and the needle protection housing are formed from a molding material that has added thereto a specific color pigmentation preassigned, pursuant to ISO standard, to a particular gauge of needle. With the needle of the particular gauge attached or integrated to the base or needle hub of the needle assembly, and given that both the base and the needle protection housing are of the same specific color, a user can readily ascertain the gauge of the needle by merely looking at the color of the needle assembly, i.e. either the base or the housing, or both. The needle protective housing is used to cover the needle once it is used, by being pivoted to a position in alignment substantially along the longitudinal axis of the needle assembly.

The instant invention also relates to the method of manufacturing the needle device that includes the steps of selecting a needle having a particular gauge, adding a specific color to a molding material, forming a needle assembly having a base and a needle protection housing pivotable relative to the base from the molding material so that the base and the housing have the same specific color, attaching the needle to the base, with the needle being coverable by the housing when the housing is pivoted to a position in alignment along the longitudinal axis of the base, and corresponding the specific color to the particular gauge of the needle so the user can ascertain the gauge of the needle by looking at the color of the needle assembly.

The instant invention also relates to the manufacture of a plurality of needle devices in which the respective colors are assigned to needles of different gauges. Moreover, different colored molding materials are provided and a color molding material with the color assigned to a given needle gauge is used for forming a plurality of needle assemblies each having a base and a needle protection housing pivotable relative to the base being the same specific color. Needles of the gauge that correspond to the specific color are attached to the base of the needle assemblies. When the job batch involving all of the needles of the same gauge have been attached to needle assemblies that have the color specific to the needle gauge, another job batch may begin whereby needles of a different gauge are attached to needle assemblies whose bases and needle protective housings have the same color that has been assigned to the needles with the different gauge. With the needle assemblies each being color coded to correspond to a particular needle gauge, a user can readily determine the gauge of the needle that she wants to use by merely looking at the color of the needle assembly.

The instant invention further is related to syringes to which a needle protective housing is connected, either directly or by way of a collar to the neck of the syringe. For the inventive syringes, a needle is fixedly fitted to the syringe, and it is usually covered by a needle sheath prior to its use. As is the case with non-syringe needle protection devices, different syringes have different needle sizes. For the syringe invention, the needle protective housing of the syringe is manufactured to have a color that corresponds to the gauge of the needle that is fitted to the syringe. Alternative embodiments of the syringe invention entail the manufacturer of the needle sheath to have the same color as the needle housing, so that prior to use, a syringe with a fixed needle would have both its housing and the needle sheath that covers the needle prior to use being color coded to represent the gauge of the needle of the syringe. Yet a further variation of the syringe of the instant invention entails the manufacturer of the syringe to also have the same color as the protective housing so that everything on the syringe may have the same color that corresponds to the gauge of the needle. It may well be that the needle sheath is made of clear plastic material so that the user can view the needle prior to its use.

BRIEF DESCRIPTION OF THE FIGURES

The present invention will become apparent and the invention itself will be best understood by reference to the following description of the present invention taken in conjunction with the accompanying drawings wherein.

DETAILED DESCRIPTION OF THE INVENTION

Figure 1:
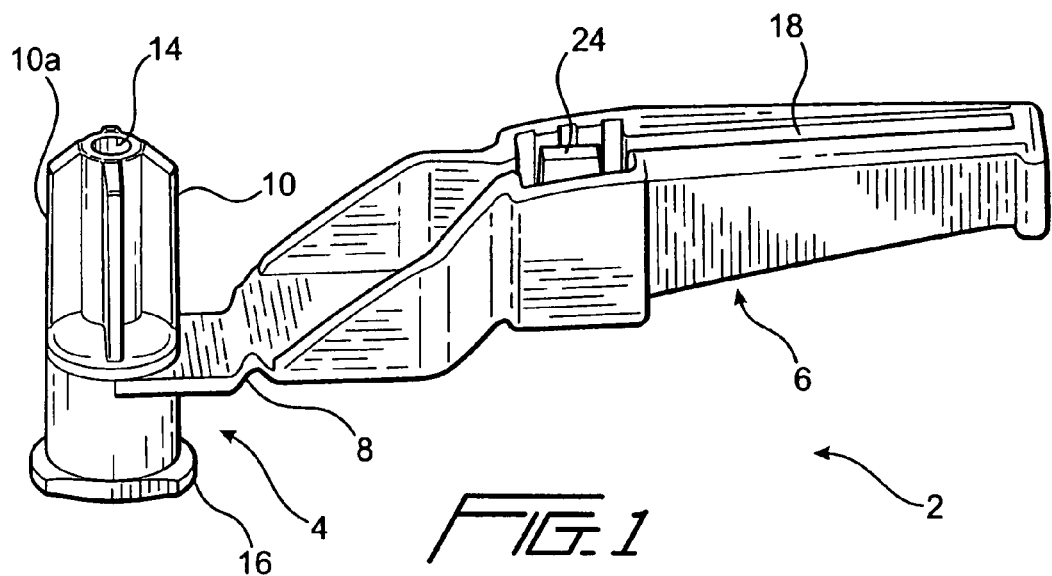
FIG. 1 is a perspective view of a needle assembly of the instant invention in which the base has attached thereto a needle protective housing.

The present invention safety needle device comprises a needle assembly 2 that has a base 4 and a protective housing 6. Base 4 is connected to protective housing 6 by a living hinge 8. Base 4 has a needle hub 10 to which a needle 12 is attached at an opening 14. Once attached, needle 12 is sealed. Needle 12 could also be integrated to needle hub 10. Base 4 further has a luer end 16 which mates with a luer end of a syringe, as is well known in the art. Protective needle housing 6, for the embodiment shown, comprises a housing that has a longitudinal slot 18 through which needle 12 passes, when housing 6 is pivoted in the direction as shown by directional arrow 20 toward the longitudinal axis 22 of base 4 for enveloping or covering needle 12. A needle retention mechanism such as a hook 24 is provided in needle protective housing 6 for grasping needle 12, once housing 6 is pivoted to be in substantial alignment along the longitudinal axis 12. Once grasped by hook 24, needle 12 and housing 6 are retained relative to each other so that needle 12 is prevented from being further exposed. Note that instead of a hook, other needle retention mechanism such as the SIDE SNAP locking mechanism as disclosed in the afore-mentioned incorporated by reference RE 37,110 may also be used.

As best shown in FIG. 1, needle assembly 2 is a single unit that may well be injection molded from a medical plastics material such as for example polypropylene. In some instances, instead of being a single unitary unit, housing 6 and base 4 may be molded as separate units with means provided at housing 6, such as for example a ring or a collar, that allows housing 6 to be attached to base 4. In any event, housing 6 and base 4 for the embodiment shown in the drawings are parts of the same needle assembly and are injection molded from a given conventional medical plastics molding material such as for example polypropylene.

Because there are a number of different medical procedures, needle 12 may be manufactured with different dimensions, or different gauges, for example from 18 gauge to 30 gauge in conventional practice. Prior to the instant invention, a needle of a particular gauge is attached to a needle hub of a specific color. To use, the needle is mated to a luer end of a syringe. But the needle, whatever its gauge, is covered by a needle sheath such as component 26 shown in FIG. 2. Needle sheath 26 most likely is mated to needle hub 10 by frictional contact with the fins 10a that extend along the length of needle hub 10. Needle sheath 26 may well be made from an opaque plastics material so that once needle sheath 26 is fitted to needle hub 10 to cover needle 12, needle hub 10 is not readily viewable. Indeed, insofar as the major portion of needle hub 10 is covered by the base of needle sheath 26, there is but a small portion of needle hub 10 that may be viewed by the user for determining the color of the needle hub. Accordingly, the gauge of needle 12 is not readily ascertained.

The International Standard Organization (ISO) has assigned to the different gauged needles specific corresponding colors. Relying on the ISO standard, the inventors of the instant invention envision the color coding of the different gauged needles by making the complete needle assembly to which a needle is attached the specific color that is assigned to the particular gauge of the needle. In other words, assuming that a 22 gauge needle has been assigned the color "black", that 22 gauge needle would be fitted or attached to a completely black needle assembly such as for example needle assembly 2 as shown in FIG. 1. The needle assembly may be injection molded from a molding material that has added thereto a black color pigmentation. Thus, the 22 gauge needle assembly is black at both its base 4 and its protective housing 6, as well as hinge 8. Similarly, for a 23 gauge needle, the needle assembly 2 to which the 23 gauge needle is attached would be blue, insofar as it is assumed that a 23 gauge needle has been assigned the color "blue". For a 25 gauge needle, the needle assembly for that needle would be orange, pursuant to the "orange" color that has been assigned to a 25 gauge needle, etc.

With both the base 4 and the needle protective housing 6 being of the same specific color that corresponds to the gauge of the needle, a user can therefore readily determine from a glance of the needle assembly the gauge of its needle, even were the needle covered by a needle sheath 26 that is opaque. To provide a redundant means for a user to determine the gauge of the needle, needle sheath 26 may be made of a clear plastic material.

Figure 3:
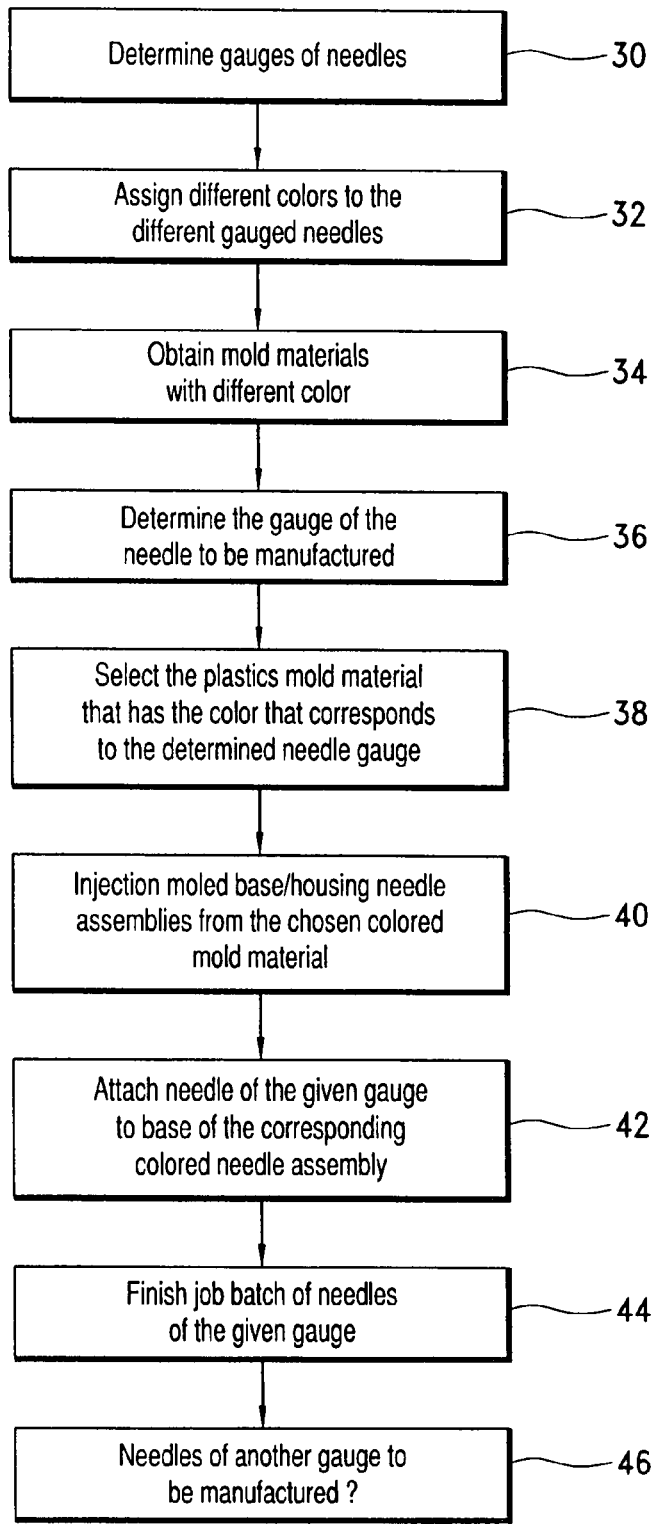
FIG. 3 is a flow chart illustrating an exemplar method of manufacturing the instant invention.

The method by which the gauge of a needle is color coded per the instant invention is discussed herein with the flow chart in FIG. 3. Assume that a plurality of needles of different gauges are to be manufactured. Further assume that there are a number of batches of needles to be manufactured, with the needles of each batch being of a particular gauge.

Figure 2:
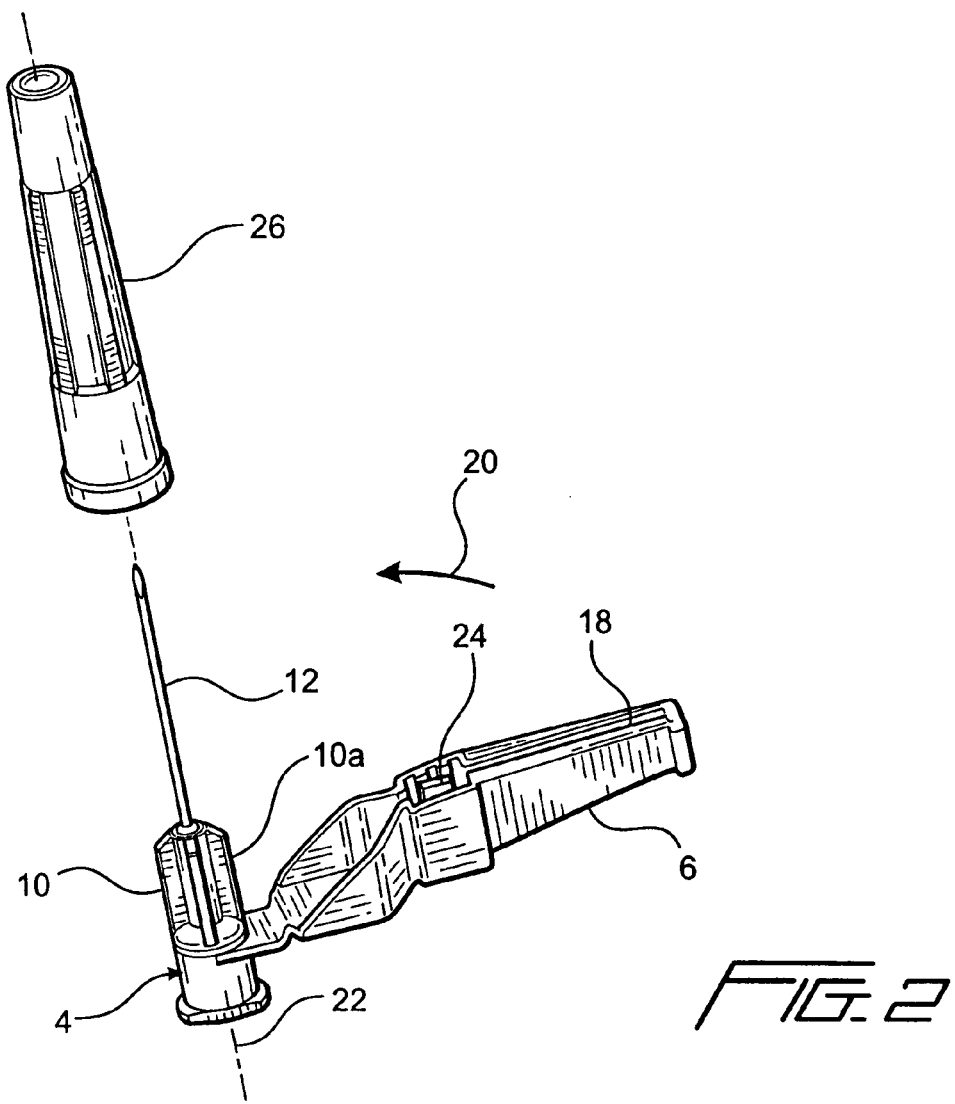
FIG. 2 is a needle assembly of the instant invention that has attached to its base or needle hub a needle of a gauge that corresponds to the color scheme of the needle assembly.

Starting at step 30, the process of the instant invention begins by determining the gauge, or gauges, of the needles to be manufactured. At step 32, different colors are assigned to the different gauged needles. At step 34, molding materials of different colors are obtained. Assume that for the manufacturing process, a batch of needles each having the same particular gauge are to be manufactured. That being the case, at step 36, the gauge of the batch of needles that are to be manufactured is determined. Thereafter, the molding material that has the color that corresponds to the determined gauge of the needle is selected, per step 38. With the appropriately colored molding material now selected, the process proceeds with the injection molding of the needle assembly, for the embodiment comprising both the base and the housing as a single unit, from the chosen colored molding material, per step 48. This injection molding process may be performed by a number of conventional injection molding machines such as for example the injection molding machines manufactured by the Nissei Company of Japan. With the molded needle assemblies on hand, the needles of the same particular gauge each are attached to the base, or the needle hub of the base, of one of the color coded needle assemblies, as shown in FIG. 2, per step 42. At the end of the manufacturing process after step 42, a needle assembly that has a needle of a particular gauge with a base and a housing both having the same specific color that corresponds to the gauge of the needle, such as that shown in FIG. 2, is produced. Thereafter, a determination is made per step 44 to see whether all of the needles of the same particular gauge have been assembled to corresponding needle assemblies for that job batch. And if it is determined that the job batch is finished, the process proceeds to step 46 where it is further determined whether there are other needles of other particular gauges that need to be manufactured. If there are, then the process once again proceeds as outlined above starting at step 36. On the other hand, if there are no other color coded needle assemblies to be produced, then the manufacturing process is stopped.

It should be appreciated that even though the needle sheath as disclosed above is made of either an opaque material or a clear plastics material, it may well be that the needle sheath may also be made of a material that may have the same color as, or a different color than, that of the base and protective housing of the needle assembly. Furthermore, even though the needle assembly as shown in FIGS. 1 and 2 is formed as a unitary unit, it may well be that the base and the protective needle housing may be formed as separate units from different molds and be connected later during the manufacturing process. If the needle sheath were also molded from the same colored molding material as the base and the needle protection housing, the needle sheath that covers the needle prior to its use may therefore also be color specific to the particular gauge of the needle.

Figure 4:
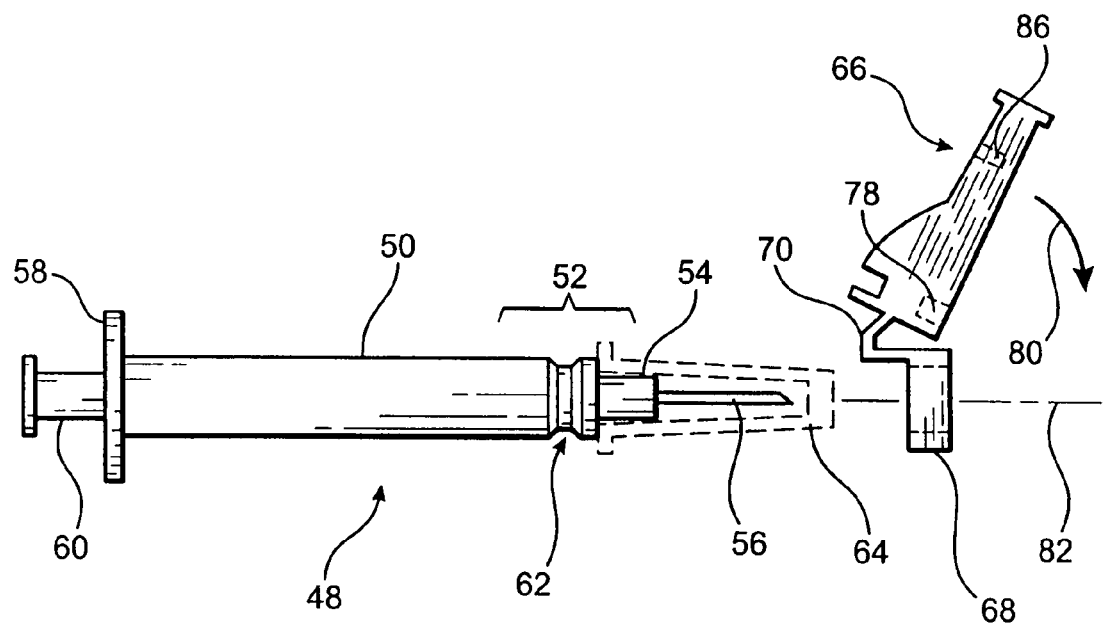
FIG. 4 is a side view of a fixed needle syringe modified to receive the collar of a needle protective housing.
Figure 5:
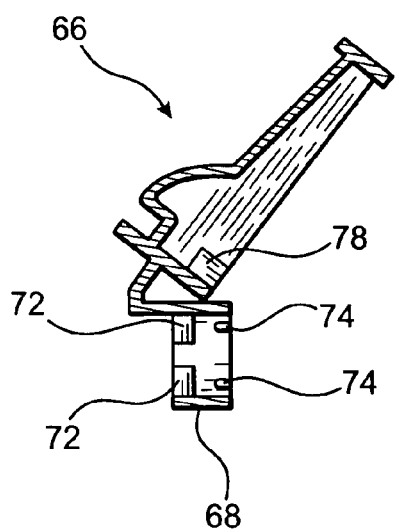
FIG. 5 is a section view of the needle housing shown in FIG. 4.
Figure 6:
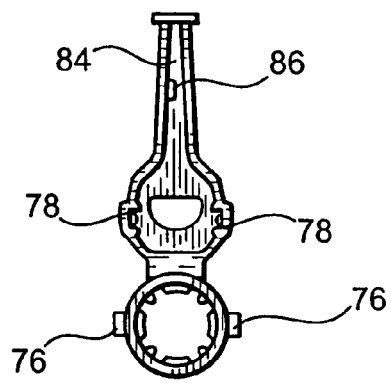
FIG. 6 is a front view of the needle housing of FIG. 4.

With reference to FIGS. 4-6, a fixed needle syringe 48 is shown to include a syringe barrel body 50 that includes a distal portion 52. A needle hub 54 at the distal portion 52 of the syringe has fixedly extending therefrom a needle 56. A finger flange 58 is provided at the proximal portion of the syringe, with a plunger 60 movably mated to the syringe barrel 50, as is well known in the art.

At the distal portion 52 of the syringe 58 there is formed a groove 62. Prior to use, needle 56 is covered by a needle sheath 64 that is frictionally held to hub 54 of syringe 48.

A needle protection housing 66 that has a base or collar 68 connected thereto by a flexible hinge 70 is fitted about syringe 48 at groove 62. Collar 68, as best shown in FIGS. 5 and 6, has a number of flanges 72 formed at its inner circumferential surface. A number of protrusions are also formed at the inner surface of collar 68. Two extensions or fingers 76 are formed at the opposite sides of the outer surface of collar 68. These fingers 76 coact with corresponding catches 78 formed at the base of housing 66, when housing 66 is pivoted in the direction as indicated by directional arrow 80, to align along the longitudinal axis 82 of collar 68 and syringe 48, as shown in FIG. 4.

When collar 68 is fitted to syringe 48, flanges 72 are matingly fitted to groove 62. The dimension of the inside diameter and more particularly the circumference formed by flanges 72 is such that it is slightly larger than the diameter of groove 62, so that collar 68 is rotatable about groove 24 after being press fitted thereto. Protrusions or bumps 74 are designed to be in contact with the syringe barrel 50 so as to provide additional friction between collar 68 and syringe 48, so that collar 68 is rotatable relative to syringe barrel 48 only if a predetermined torque is applied against collar 68, or housing 66, for rotating collar 68 relative to syringe 48.

After needle sheath 64 is removed from syringe 48, to cover the now exposed needle 56, housing 66 is pivoted in the direction of arrow 80 so that it becomes substantially aligned along the longitudinal axis 82 for covering needle 56, when needle 56 passes through slot 84 of housing 66. A hook 86 in housing 66 grasps needle 56 at this time so to prevent needle 56 from being further exposed. At the same time, housing 66 is retained to collar 68 by the interaction between catches 78 and fingers 76.

To ensure that a user can readily ascertain the gauge of needle 56 of the fixed needle syringe, housing 66, as well as collar 68 are molded from a plastics material such as that discussed earlier so that the color of the housing 66 and collar 68 would have the same color as that given in the common ISO standard that corresponds to the gauge of needle 56, as noted earlier. For example, a 22 gauge needle would have a housing that is black, a 23 gauge needle would have a housing that is blue, and a 25 gauge needle would be orange, etc.

Figure 7:
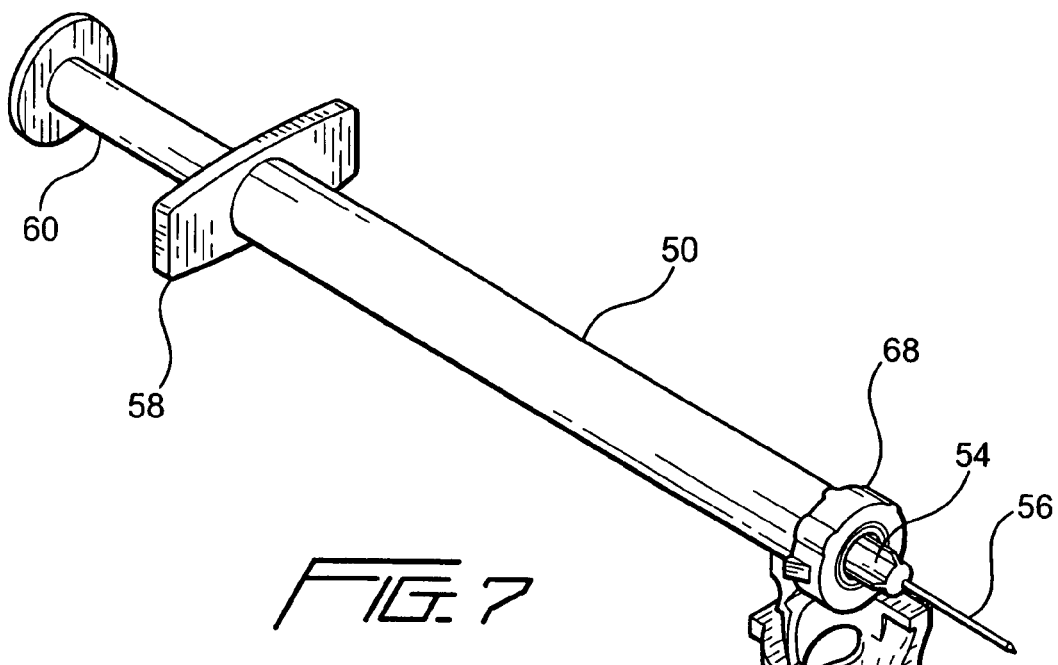
FIG. 7 is a perspective view of the syringe of FIG. 4 with the needle sheath removed showing an exposed needle.
Figure 8:
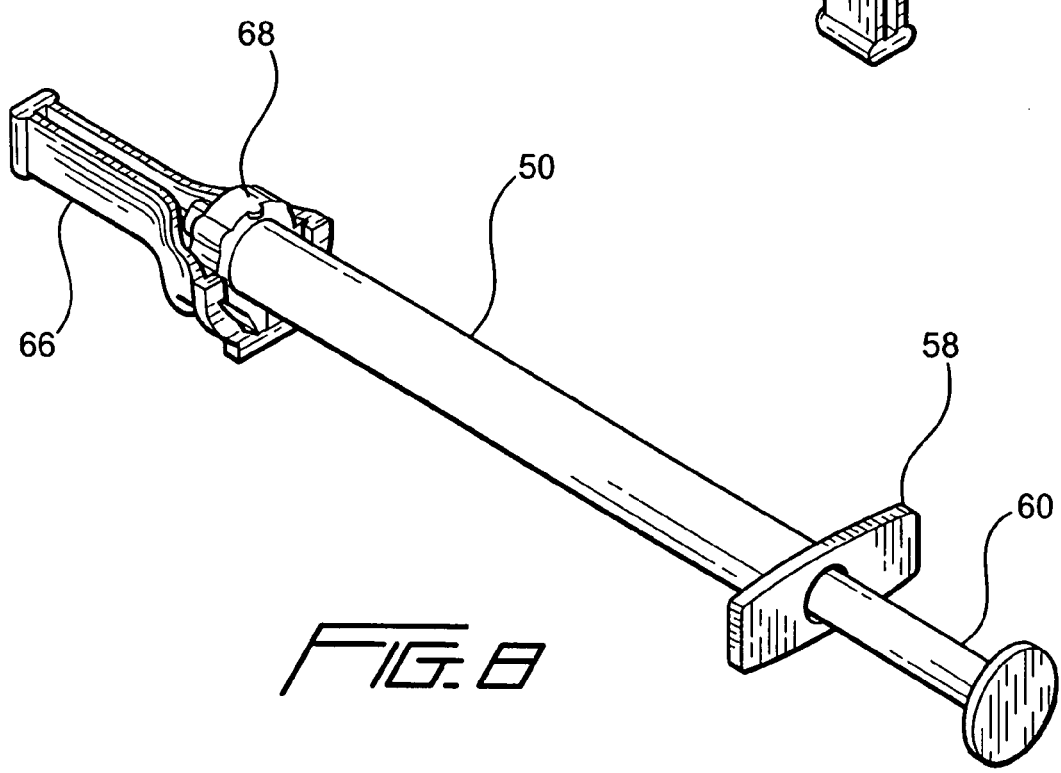
FIG. 8 is a perspective view of the syringe of FIG. 7 with the exposed needle covered by the needle housing.

For the FIG. 4 embodiment, instead of being clear, needle sheath 64 may also be molded or formed from a plastics material that has a color that corresponds to the gauge of the needle. Such needle sheath therefore enables a user to readily ascertain the gauge of the needle, even before the user removes the needle sheath from the syringe. Alternatively, as was noted before, needle sheath may be made from a clear plastics material or a translucent material. FIGS. 7 and 8 provide perspective views of the fixed needle syringe of the instant invention, with FIG. 7 showing the exposed needle 54 and FIG. 8 illustrating needle 54 being covered by housing 66.

Although the embodiment illustrated in FIGS. 4-8 shows a fixed needle syringe that has attached thereto a housing via a rotatable collar, a fixed needle syringe could have a housing integrally or directly formed with the syringe, so that the housing is not rotatable relative to the syringe. For that embodiment, both the syringe barrel and the housing would be manufactured from a plastics material that has added thereto the color pigmentation that corresponds to the gauge of the needle to be fixed to the syringe. In other words, aside from possibly plunger 60, the body of the syringe barrel, as well as the needle housing, would be color coded to correspond to the gauge of the needle to which the particular syringe is fitted. It should be appreciated however that plunger 60 may also be color coded to the needle gauge. For this embodiment, needle sheath 64 may be made of the same color coded molding material so that it too is color coded to correspond to the gauge of the needle of the syringe.

The manufacturing of a fixed needle syringe of the instant invention begins with a determination of the gauge of the needle that is to be fitted to the syringe, either individually or for the batch of the same needle gauge syringes that are to be manufactured. The specific color that corresponds to the gauge of the needle is then determined according to a given standard, such as the ISO Standard. Appropriate color pigmentation is next added to the material to be used for forming the mold. In the case of the syringe as shown in FIGS. 4-8, the housing is formed with a base, or a collar, that is to be fitted to the syringe. In this case, the syringe barrel itself may be formed from a different plastics material, or be formed from the same color coded material so as to have the same color as the housing and the base. Once the housing is formed, it is fitted to the syringe barrel via the collar, so that it is rotatable relative to the syringe barrel. With the housing thus color coded, a user can readily ascertain the gauge of the needle, even when the needle sheath that covers the needle prior to use is made of a clear or translucent material. To further enhance the determination of the gauge of the needle of the syringe, the needle sheath that covers the syringe prior to use may also be manufactured to have the same color as the housing.

For the case where the needle housing is integrally formed with the syringe from a mold, both the housing and syringe would naturally have the same color that corresponds to the gauge of the needle. Of course, the needle sheath that covers the needle prior to use may likewise have the same color as the housing.

Figure 9:
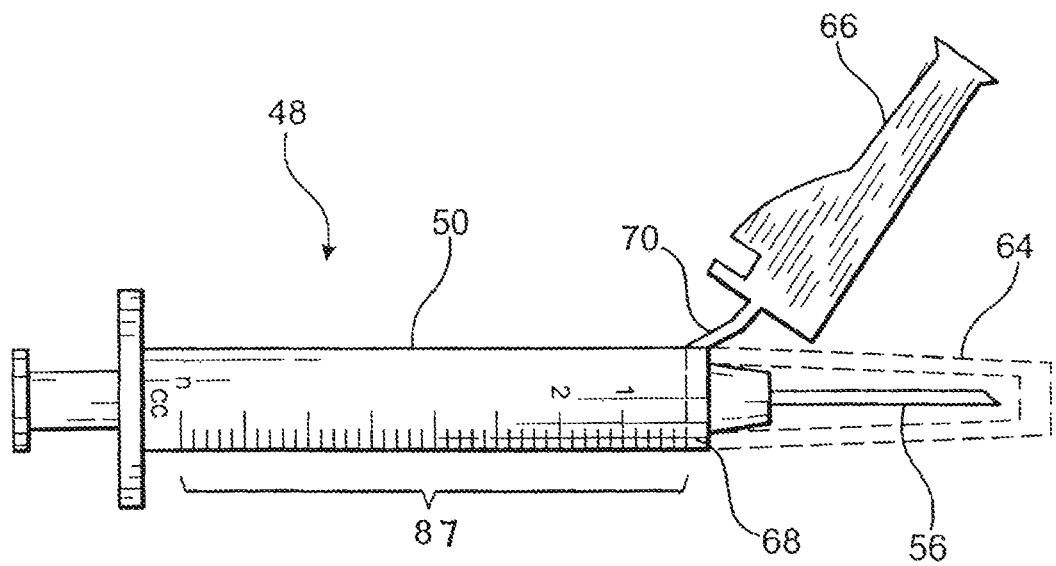
FIG. 9 is cross-sectional view of syringe having attached thereto a needle protective housing and markings with a color that corresponds to the gauge of the needle.

FIG. 9 is an illustration of an alternative embodiment of the instant invention in which markings 87 are provided on syringe barrel 50 in a color that corresponds to the gauge of the needle 56. For this embodiment, housing 66 may be directly attached to the syringe 48 by way of living hinge 70, or as was the case for the FIG. 4 embodiment, attached by way of a collar 68 shown in dotted line. In the case were housing 66 is an integral part of syringe 48, as for example by being manufactured from the same mold during the same operation, housing 66 may have the same color as syringe barrel 50, or may in fact be clear. Yet by using a color coded marking such as the scales 87 printed directly on syringe barrel 50, a user can readily ascertain the gauge of the needle 56 by the color of the markings. Markings 87 in fact provide multiple functions in that, in addition to informing the user at a glance the gauge of the needle, they, being in the form of scales that are printed onto the body of the syringe, also enable a user to ascertain the volume of fluid in the syringe.

For the case where housing 66 is coupled to syringe 48 by way of a collar 68, housing 66 as well as collar 68 are color coded to reflect the gauge of needle 56 that is fixed to syringe 48. Needle sheath 64 could either be clear, translucent, or color coded to correspond to the gauge of the needle 56. Thus, for the FIG. 9 embodiment, the syringe, prior to use, may have a conventional syringe barrel, but with markings and its needle protective housing being color coded to indicate the gauge of the needle that is covered by the needle sheath. The needle sheath may also be color coded. Alternatively, the syringe barrel as well as the needle protective housing may be non-color coded, while the markings are color coded to indicate the gauge of the needle. In this alternative embodiment, the needle sheath may or may not be color-coded. Markings 87 may be added to syringe barrel 50 by a conventional printing process.

Figure 10:
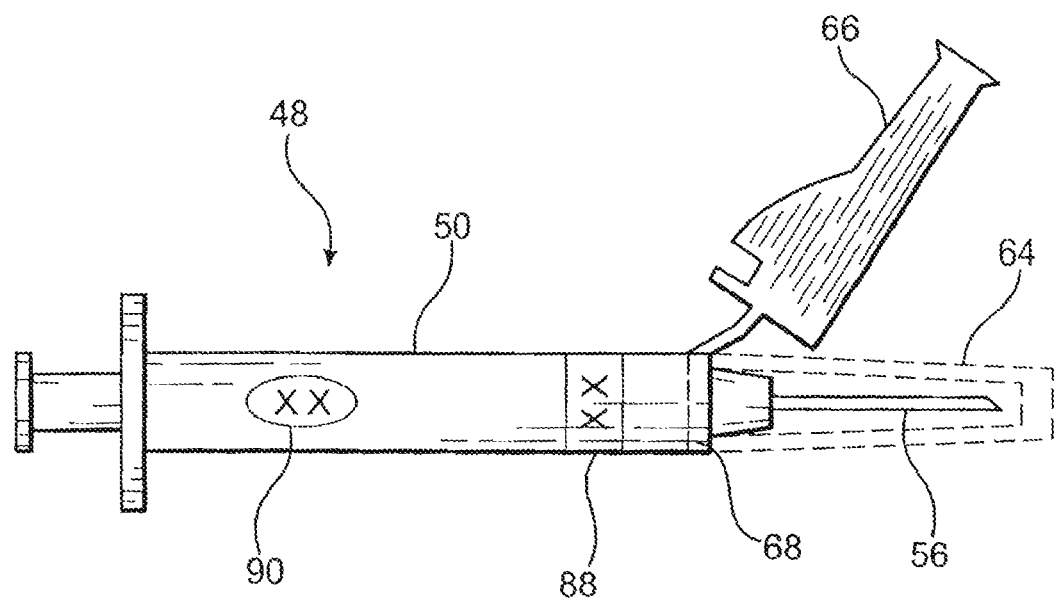
FIG. 10 illustrates a fixed needle syringe that has a marking in the form of a ring, or lines, at the barrel of the syringe and a decal that may be added to, or replaces the ring, at the syringe barrel.

FIG. 10 shows a fixed needle syringe that, instead of markings, has a color coded ring or band, or lines 88 printed on the syringe barrel 50. The band or lines may be in addition to the markings or scales that are printed onto syringe barrel 50, and may be located on the syringe barrel in such a way so as not to interfere with the scale markings that indicate the amount of fluid in syringe 48. The number of the gauge that corresponds to the thickness of needle 56 may be printed onto the band, as indicated by XX. The color coded band 88 may be printed on barrel 50, using a process that is used to conventionally print the markings or scales onto syringe barrel 50.

In place of, or in addition to, a color coded band or ring(s), a decal 90 may be adhesively attached to, or printed on, syringe barrel 50 at a location that does not interfere with the graduating scale markings that are ordinarily printed onto a syringe barrel. Decal 90 is color coded to indicate the gauge of needle 56. In addition, the number of the gauge of the needle may be printed onto decal 90, as indicated by "XX". For the FIG. 10 fixed needle syringe, only a color coded decal or lines or band(s) may be used to indicate the gauge of the needle. Alternatively, housing 66 attached to syringe 48 may also be color coded. Likewise, sheath 64 may also be color coded to reflect the gauge of needle 56.

The invention claimed is:

1. A needle syringe device, comprising: a syringe barrel body that includes a distal portion having a needle hub with a distal end wherefrom a needle of a particular gauge fixedly extends so that the needle is not removable from the syringe barrel body, a needle protection housing having a slot formed substantially along its body pivotable relative to said syringe barrel body, said needle having a longitudinal axis and being covered by a sheath frictionally held to the needle hub at the distal portion prior to use and is ready for use with the removal of said sheath, the sheath being made of either a translucent or clear plastic material, said needle adapted to be covered by said housing after the removal of said sheath when said housing is pivoted relative to the distal portion from a position away from the syringe barrel body to a position in alignment along the longitudinal axis of said needle, said needle passing through the slot formed along said housing when said housing is pivoted to the position to cover said needle, said housing formed from a plastics material having a specific color preassigned to correspond to said particular gauge of said needle according to a standard so that the gauge of the needle of said syringe is ascertainable by the color of said housing prior to and after the removal of said sheath to expose said needle, the needle hub having the same specific color, wherein a user is able to determine the particular gauge of the needle through the sheath without removal of the sheath because the sheath is made of the translucent or clear plastic material.

2. Syringe device of claim 1, wherein a groove is circumferentially formed about an outer surface of the distal portion away from the needle hub, and wherein said housing is connected to a collar rotatably mounted about the groove at the distal portion so that the collar is rotatable about the syringe barrel body, a number of protrusions formed at the inner circumferential surface of the collar designed to be in contact with the syringe barrel body so that the collar is rotatable relative to the syringe barrel body only if a predetermined torque is applied against the collar or housing to rotate the collar and housing relative to each other.

3. Syringe device of claim 2, wherein the barrel body of said syringe has the same color as said housing, the gauge of said needle being ascertainable by the color of said housing and/or the barrel body of said syringe.

4. Syringe device of claim 1, wherein said housing is integrally formed with said syringe, wherein the syringe barrel body has the same specific color as the housing.

5. A needle syringe device, comprising: a syringe barrel body having a longitudinal axis and a needle of a given gauge fixedly extending from a closed end of a needle hub at a distal portion of the syringe barrel body, the needle not removable from the syringe barrel body, a groove circumferentially formed at an outer surface of the distal portion away from the needle hub, the hub covered by a sheath made of either a translucent or clear plastic material before use, at least one color coded marking of a color determined to correspond to the given gauge of the needle in accordance with a predetermined standard provided on at least a portion of the barrel body of the syringe, a housing having a collar rotatably fitted to the groove at the distal portion of the barrel body of said syringe, a number of protrusions formed at the inner circumferential surface of the collar designed to be in contact with the syringe barrel body so that the collar is rotatable relative to the syringe barrel body only if a predetermined torque is applied against the collar or housing to rotate the collar and housing relative to each other, the housing pivotable relative to the distal portion of the barrel body of said syringe to be in alignment along the longitudinal axis of the barrel body for covering the needle after said sheath is removed from the hub of said syringe, the gauge of the needle being determinable at all time by looking at the color of the marking on the barrel body of the syringe, the marking being printed on or adhered to the barrel body of said syringe, the given gauge of the needle can be redundantly determined through the sheath because the sheath is made of the translucent or clear plastic material.

6. Syringe device of claim 5, wherein said housing has the same color as said marking.

7. Syringe device of claim 5, wherein said marking comprises volume amount indications of said syringe printed on the barrel body of said syringe.

8. Syringe device of claim 5, wherein said marking comprises a decal attached to said syringe barrel body that has the color determined to correspond to the gauge of said syringe.

9. Syringe device of claim 8, wherein said decal has printed thereon the gauge number of the needle.

10. Syringe device of claim 5, wherein said marking comprises at least one color coded band on the barrel body of said syringe, the color of said band corresponding to the given gauge of the needle.

11. Syringe device of claim 10, wherein said band has printed thereon the gauge number of the needle.

12. A needle syringe device comprising:
 a syringe barrel body having a distal portion including a needle hub with a closed end;
 a needle of a given gauge fixedly extending from the closed end of the needle hub so that the needle is not removable from the syringe barrel body;
 a sheath frictionally fitting over the needle hub for covering the needle before its use, the sheath made of either a translucent or clear plastic material, the needle being usable once said sheath is removed from the needle hub;
 a needle protection housing connected to and pivotable relative to said syringe barrel body from a position away from the barrel body to a position substantially in alignment with the barrel body to cover said needle when said housing is pivoted to a position in alignment along the longitudinal axis of said needle;
 wherein said syringe barrel body and said housing are coded in a color that identifies the given gauge of said needle in accordance to a standard at all times.

13. Syringe device of claim 12, wherein the syringe barrel body has a groove circumferentially formed about an outer surface of the distal portion away from the needle hub, and wherein said housing is connected to a collar that is mounted about the groove at the distal portion of the barrel body so as to be rotatable about said syringe barrel body, a number of protrusions formed at the inner circumferential surface of the collar designed to be in contact with the syringe barrel body so that the collar is rotatable relative to the syringe barrel body only if a predetermined torque is applied against the collar or housing to rotate the collar and housing relative to each other.

14. Syringe device of claim 12, wherein both of said syringe barrel body and said housing are made from a molding material having the color that corresponds to the given gauge of said needle according to the standard.

15. Syringe device of claim 12, further comprising at least one marking on said syringe barrel body.

16. Syringe device of claim 15, wherein said syringe barrel body is color coded to identify the given gauge of said needle.

17. Syringe device of claim 12, wherein said syringe barrel body is color coded by at least one marking that has the color that corresponds to the gauge of said needle according to the standard.

18. Syringe device of claim 17, wherein said marking comprises at least one of a decal, scales and a band printed on said syringe barrel body.

* * * * *